United States Patent [19]

Chevallet et al.

[11] Patent Number: 5,722,399
[45] Date of Patent: Mar. 3, 1998

[54] DEVICE FOR MEASURING THE PRESSURE OF A LIQUID AND METHOD FOR REGULATING SUCH A DEVICE

[75] Inventors: Jacques Chevallet, Serezin du Rhone; Alain Frugier, Tignieu; Eric Louvet, Villefontaine, all of France

[73] Assignee: Hospal Industrie, France

[21] Appl. No.: 465,047

[22] Filed: Jun. 6, 1995

[30] Foreign Application Priority Data

Sep. 14, 1994 [FR] France ...................... 94 11216

[51] Int. Cl.$^6$ ...................................... A61B 5/00
[52] U.S. Cl. .................. 128/637; 128/672; 128/748; 73/706; 73/715
[58] Field of Search .............. 128/637, 672–673, 128/748, 685; 73/706–708, 715; 604/67

[56] References Cited

U.S. PATENT DOCUMENTS 3,863,504  2/1975  Borsanyi .
4,166,396  9/1979  Baker ........................... 73/706 X

FOREIGN PATENT DOCUMENTS 0611227  1/1994  European Pat. Off. .

*Primary Examiner*—Jennifer Bahr
*Assistant Examiner*—Ryan Carter
*Attorney, Agent, or Firm*—Finnegan, Henderson, Farabow, Garrett & Dunner, L.L.P.

[57] ABSTRACT

A liquid treatment apparatus includes a sensor which is sensitive to a variation in gas pressure and which generates signals indicative of sensed pressures. The apparatus also included a casing divided into a first compartment and a second compartment by a flexible membrane, the first compartment having at least one orifice for the introduction of the liquid, and the second compartment being connectable in a leaktight manner to the pressure sensor. A pump is provided to vary a quantity of gas in the second compartment, and a controller is provided to regulate the pump as a function of variations in pressure generated in the second compartment. The controller is configured to receive signals from the sensor and to cause, through the pump, at least two successive pressure variations, having opposite directions, in the second compartment so as to adjust said position of the membrane between a wall of the casing bounding the first compartment and a wall of the casing bounding the second compartment.

26 Claims, 2 Drawing Sheets

DEVICE FOR MEASURING THE PRESSURE OF A LIQUID AND METHOD FOR REGULATING SUCH A DEVICE

BACKGROUND OF THE INVENTION

1. Field of the Invention

The present invention relates to a device for measuring the pressure of a liquid and to a method for regulating such a device.

2. Description of the Related Art

The pressure measurement device to which the invention relates is of the type comprising a pressure sensor sensitive to the pressure of a gas and a casing divided into two compartments by a nonpermeable flexible membrane, the first compartment having at least one orifice for introducing the liquid therein and the second compartment being connectable, by leaktight connection means, to the pressure sensor. The pressure variations in the liquid are transmitted by the membrane to the gas present in the second compartment, and the pressure variations of the gas are measured via the sensor.

This type of pressure measurement device is used, in particular, in apparatuses for treating blood by extracorporeal circulation, comprising a treatment device proper, such as a dialyser or a centrifuge, to which are connected various pipes in which several liquids, such as blood, are circulated. In this type of apparatus, it is essential, for safety reasons, to check the pressure of the various liquids flowing through the pipes, which are generally single-use pipes. The apparatus is equipped with several sensors which are not disposable, with which pressure measurement casings arranged on the pipes interact during operation.

An advantage of this type of measurement device for measuring blood pressure is that it makes it possible to avoid any interface between blood and air and, thereby, the appearance of coagulated blood filaments such as may be observed in bubblers arranged on extracorporeal blood circulation circuits after two or three hours of use.

On the other hand, however, the membrane may sometimes come to bear during use against one or other of two opposite walls of the casing (depending on whether the liquid is in overpressure or under reduced pressure with respect to the atmosphere), making the device incapable of detecting pressure variations. A slight gas leak at the connection between the second compartment and the pressure sensor may the cause of this malfunction. It is here assumed that, at least with some types of membrane, this might also be caused by gas permeating from the first compartment to the second compartment, through the membrane. This progressive impairment of the operation of the device cannot be detected using a simple pressure measurement, since the pressure may remain within a pressure margin which is judged acceptable even when the membrane is no longer responding.

European Patent Application no. 0 611 228 describes a method for detecting when the membrane has come to bear on a wall of the casing and the pressure measurement device is inoperative. According to this application, in order to detect whether the membrane is still operational, an instantaneous variation in the flow rate of the liquid circulating in the first compartment is caused at given time intervals, the variation in pressure in the second compartment as a function of time is calculated and this variation is compared with a predetermined value corresponding to the response of an operational membrane.

When it is detected that the pressure measurement device is inoperative, the problem which arises is to rectify the anomaly without having to change the pipe on which the defective casing is arranged. This problem seems not to have been identified as such until now.

SUMMARY OF THE INVENTION

One object of the invention is therefore to produce a pressure measurement device of the type mentioned hereinabove, whose measurement remains reliable irrespective of the length of time for which it has been used.

In order to achieve this object, a pressure measurement device is provided according to the invention which is characterized in that it comprises means for positioning the membrane in a determined position in the casing. These means may comprise means, such as a pump, for varying the quantity of gas in the second compartment, and control means for driving the pump so as to adjust the position of the membrane between a wall of the casing bounding the first compartment and a wall of the casing bounding the second compartment.

This device provides two substantial advantages, one therapeutic and the other financial, which are even more substantial because it forms part of a machine/disposable treatment module assembly as described in European Patent Applications no. 0 611 228 and no. 0 611 227. It will be recalled that the disposable treatment module forming the subject of one of these applications comprises a blood treatment apparatus (haemodialyser, for example) to which multiple pipes are connected, some of which comprise pressure measurement casings having membranes. By virtue of the device according to the invention, this highly integrated module can be changed only when the blood treatment apparatus requires to be changed, and its working life is not limited by possible malfunction of a pressure measurement device. This is advantageous for therapy insofar as the operations of disconnecting and connecting an extracorporeal blood circulation circuit to the patient always involve risks, especially of contamination. From the financial point of view, the advantage will immediately be seen of being able to use disposable treatment modules up to the limit imposed by the blood treatment apparatus itself.

Another advantage of this device is that it makes it possible to economize on means for detecting lack of reaction by the membrane.

According to one characteristic of the invention, the means (pump) for varying the quantity of gas in the second compartment of the casing are connectable to this compartment by a pipe which can be closed by a valve and a second pressure sensor is connected to the pipe portion joining the valve to the pump. Means are provided for comparing the data measured by the first and second pressure sensors and for driving the pump so that the pressures in the pipe on either side of the valve can be made substantially equal.

By virtue of this arrangement, it is possible to prevent the membrane from being subjected to intense pressure variations during each regulating phase.

A further subject of the invention is an apparatus for treating blood by extracorporeal circulation, comprising several pressure measurement devices which are connected to a single pump by connection means allowing successive regulation of the position of the membranes in the various casings.

A further subject of the invention is a method for regulating a pressure measurement device of the type mentioned hereinabove, comprising the steps of:

introducing the liquid whose pressure is to be measured into the first compartment;

measuring the pressure of the gas in the second compartment;

adjusting the quantity of gas in the second compartment so that the second compartment contains a quantity of gas corresponding to a determined position of the membrane in the casing.

According to one characteristic of the invention, the step of adjusting the quantity of gas in the second compartment comprises the steps of:

varying the quantity of gas in the second compartment in one sense until the pressure of the gas reaches a first determined threshold value;

varying the quantity of gas in the second compartment in the opposite sense until the pressure of the gas reaches a second determined threshold value;

again varying the quantity of gas in the second compartment in the opposite sense so that the second compartment contains a quantity of gas corresponding to a determined position of the membrane in the casing.

BRIEF DESCRIPTION OF THE DRAWINGS

Other characteristics and advantages of the invention will emerge on reading the following description. Reference will be made to the attached drawings, in which.

DESCRIPTION OF THE PREFERRED EMBODIMENTS

Figure 1:
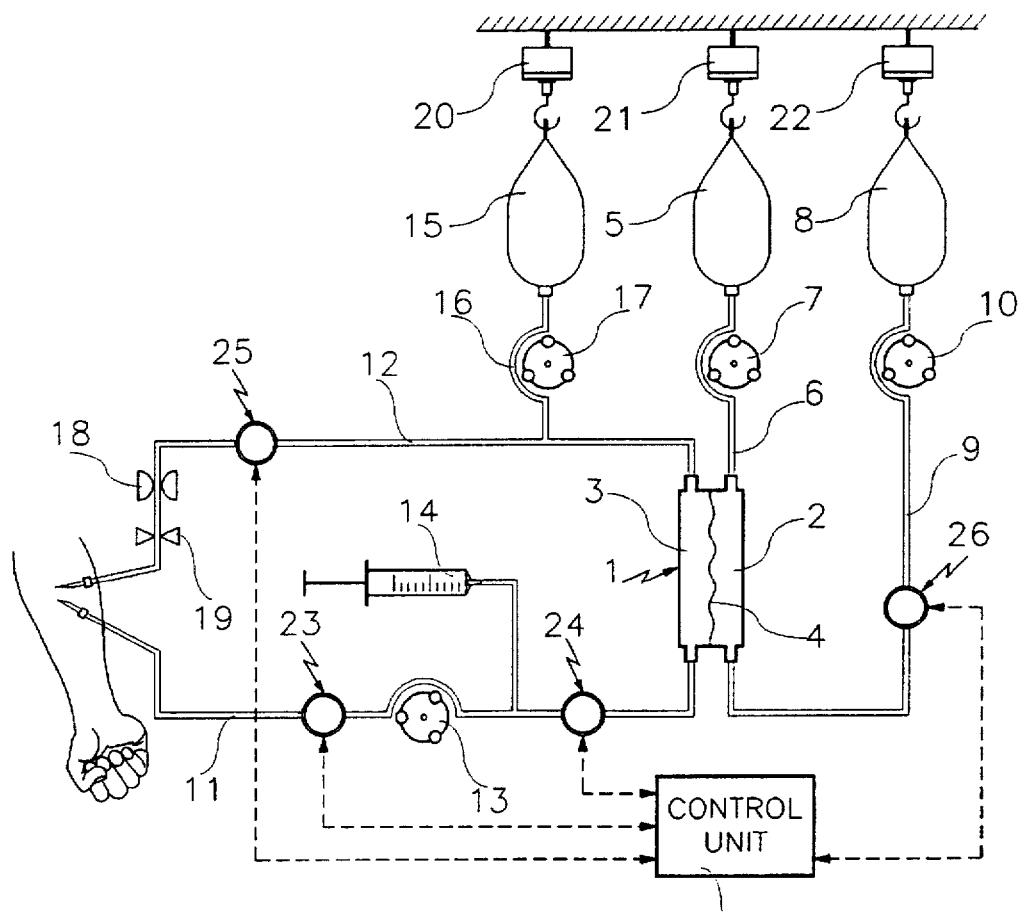
FIG. 1 is a schematic diagram of a blood treatment apparatus comprising a plurality of pressure measurement devices according to the invention.

FIG. 1 illustrates an apparatus for treating blood by extracorporeal circulation, and with which several types of treatment can be administered, in particular dialysis, haemofiltration and haemodiafiltration. This apparatus comprises an exchanger 1 with semipermeable membrane, such as a dialyser or a haemofilter, having two compartments 2, 3 separated by a semipermeable membrane 4. A first compartment 2 has an inlet connected to a bag 5 of treatment liquid (dialysis liquid) via a supply pipe 6 on which a supply pump 7 is arranged, and an outlet connected to a bag 8 for collecting spent liquid, via a discharge pipe 9 on which an extraction pump 10 is arranged. The second compartment 3 is connected to an extracorporeal blood circulation circuit comprising a withdrawal pipe 11 having a cannula at one end and being connected, at its other end, to an inlet of the second compartment, and a return pipe 12 having a cannula at one end and being connected, at its other end, to an outlet of the second compartment 3. A circulation pump 13 is arranged on the withdrawal pipe 11. A device 14 for injecting anticoagulant is connected to the withdrawal pipe 11 downstream of the circulation pump 13. A bag 15 of substitution liquid is connected to the return pipe 12 via a perfusion pipe 16 on which a perfusion pump 17 is arranged. A bubble detector 18 and a closure member 19 are placed on the return pipe 12, in proximity to the cannula. The three bags 5, 8, 15 are suspended from scales 20, 21, 22 making it possible to keep account of the liquids circulated with a view to a determined therapeutic aim.

For more details on this apparatus and its operation, reference will be made to European Patent Application no. 0 611 228 and to European Patent Application no. 0 611 227 which respectively describe an apparatus of this type and a single-use liquid treatment module particularly suited to this apparatus.

The apparatus which has just been described in brief is intended for treating so-called "acute" patients who, in contrast to so-called "chronic" patients, for whom each treatment session lasts only a few hours, may require treatment sessions lasting several days. It is therefore of the greatest importance to provide this type of apparatus with liquid pressure measurement means which do not have the drawbacks mentioned hereinabove, that is to say that they do not require the hydraulic circuit to be replaced more often than is necessary from the therapeutic point of view.

The apparatus of FIG. 1 is equipped with four liquid pressure measurement devices 23, 24, 25, 26, arranged respectively on the withdrawal pipe 11, upstream and downstream of the circulation pump 13, on the return pipe 12 and on the discharge pipe 9. These devices supply pressure data to a computation and control unit 27 which drives each of these devices on the basis of the data supplied and of a regulating program previously loaded into memory. The specific functions of this control unit will be detailed hereinbelow.

Figure 2:
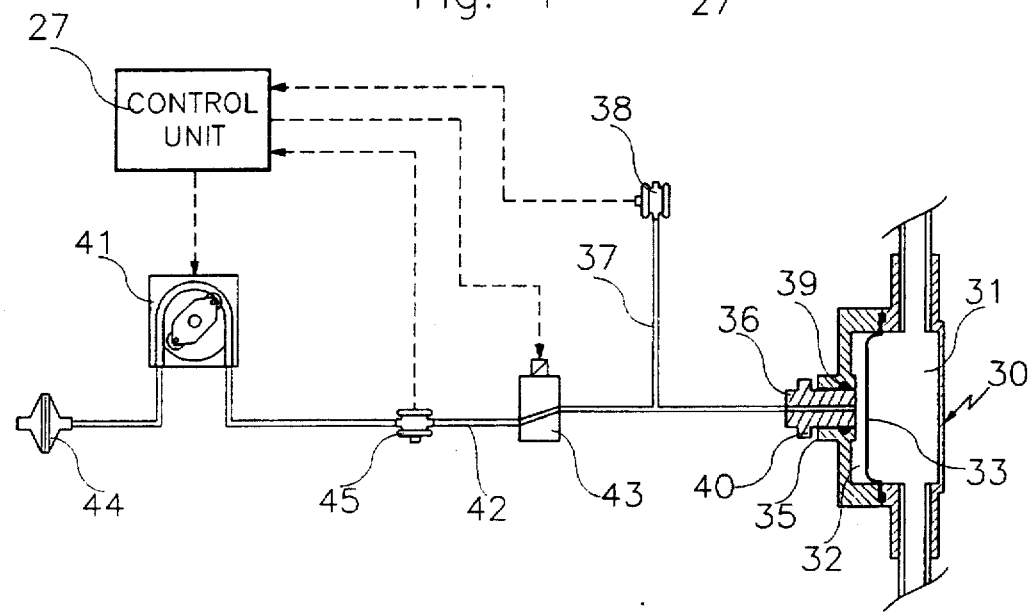
FIG. 2 is a partial cross-sectional view, of one embodiment of the apparatus of the invention.

FIG. 2 represents one of the pressure measurement devices according to the invention. This device comprises a cylindrical casing 30 which is divided into two compartments 31, 32 by a flexible circular membrane 33 made, for example, of silicone. The membrane 33 has two concentric zones joined by a rounded intermediate strip, a peripheral zone by which the membrane 33 is attached to the casing 30 and a central zone which, when the membrane is at rest, is laterally offset with respect to the peripheral zone. The membrane 33 is usually mounted in the casing so as to have a maximum excursion as a function of the mean pressures prevailing in the liquid pipe (overpressure or reduced pressure with respect to the pressure of the gas in the second compartment 32, which is generally atmospheric pressure). In FIG. 2, the mounting of the membrane 33 is suitable for a pipe in which there is a reduced pressure (case of the device 23). The first compartment 31 of the casing 30 has an inlet and an outlet which are connected to the pipe in which the liquid whose pressure is to be measured is circulating. The wall of the casing 30 bounding the second compartment 32 comprises a central orifice 34 surrounded by an outer cylindrical shoulder 35. The shoulder 35 constitutes connection means for interaction with a complementary connection tube 36 forming the end of a pipe 37 connected to a pressure sensor 38 which is sensitive to the gas pressure. This pressure sensor 38 consists, for example, of a deformable semiconductor wafer. The tube 36 comprises an end portion having an external diameter smaller than the internal diameter of the cylindrical shoulder 35; an O-ring seal 39 mounted in a circular rib made in the end portion of the tube; and a radial shoulder 40 which projects from the tube 36 and is intended to limit penetration of the tube 36 into the cylindrical shoulder 35 of the casing 30. The size of the O-ring seal 39 is chosen so that, once the casing 30 has been fitted onto the tube 36 and the cylindrical shoulder 35 is bearing against the radial shoulder 40, the connection of the compartment 32 to the tube 36 is leaktight.

According to the invention, the pressure measurement device comprises means for positioning the membrane 33 in a determined position in the casing 30. In the embodiment represented, these means comprise a peristaltic pump 41 capable of sucking or delivering air through a pipe 42 connected to the pipe 37 via a valve 43 allowing selective connection of the pump 41 and the second compartment 32 of the casing 30. The free end of the pipe 42 is equipped with a filter 44. A regulating pressure sensor 45 is arranged on the pipe 42.

Figure 3:
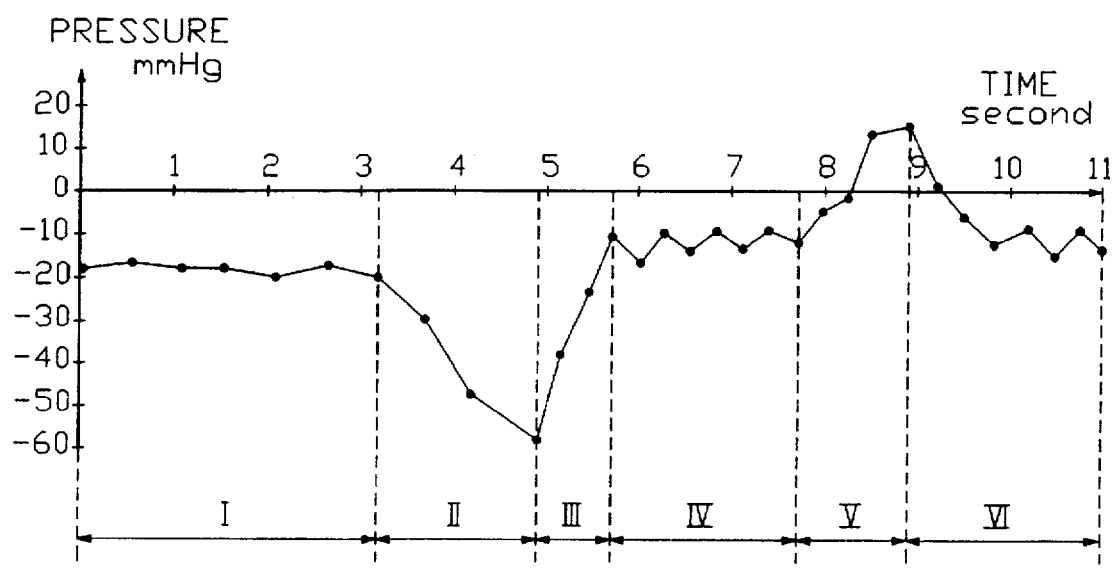
FIG. 3 is a graph illustrating a method of regulating the device according to the invention.

Reference will be made to FIG. 3 in order to follow the explanation of the operation of the device of FIG. 2.

In normal operation, the valve 43 is closed. The pressure sensor 38 continuously emits a signal representing the pressure of the liquid circulating in the first compartment 31 of the casing 30. After processing in an electronic circuit, the signal is supplied to a control unit where it is used essentially for purposes of monitoring and safety.

At regular time intervals, a phase of regulating the device is carried out, which phase consists in repositioning the membrane 33 in an optimum position from the position which it then occupies. A preparatory step for this regulating phase consists in comparing the responses of the two pressure sensors 38 and 45 and in adjusting, if required, the pressure in the pipe 42 by means of the pump 41, so that this pressure is substantially equal to the pressure in the second compartment 32. In this way, when the valve 43 is open, the membrane 33 is not subjected to any pressure variation, which might be the case if this initial pressure balancing step were not carried out. After opening the valve 43, the pump 41 is set in rotation in one sense or the other—here so as to take air out of the compartment 32. So long as the membrane 33 has not stuck against the wall of the casing 30 bounding the compartment 32, the pressure measured by the sensor 38 remains substantially constant (period I). When the o membrane 33 has stuck against the wall, the measured pressure decreases rapidly (period II). When the pressure reaches a bottom threshold value previously stored in the control unit 27, the sense of rotation of the pump 41 is reversed, that is to say that air is introduced into the compartment 32. The pressure increases rapidly s (period III) then reaches a plateau (period IV) corresponding to a floating position of the membrane 33. Starting from the time when the membrane 33 bears against the wall of the casing 30 bounding the first compartment 31, the pressure again increases (period V). When the pressure reaches a top threshold value previously stored in the control unit 27, the sense of rotation of the pump 41 is again reversed for a predetermined period of time which corresponds to an optimum position of the membrane 33 in the casing 30. When the flow rate of the pump 41 is regulated to be constant, whether the pump 41 is operating in suction or in delivery, this predetermined period of time can be calculated to be equal to a portion of the time (half the time, for example) which has elapsed between the two consecutive reversals of the sense of rotation of the pump 41, that is to say a portion of the sum of the periods III, IV and V.

The bottom and top threshold values mentioned hereinabove are preferably calculated in terms of variation from the pressure value measured in the chamber 32 before the start of the device regulating phase which has just been described.

The position of the membrane 33 can be regulated in various ways, of which the one which has just been described is only one example. In particular, in the above described method, it is assumed that at the starting up of each regulating phase, the membrane 33 is in a floating position corresponding to a plateau pressure. This assumption is correct as long as the frequency of the successive regulating phases is high so that, even if the casing 30/pressure sensor 38 arrangement is leaking or the permeation of gas through the membrane 33 is important, the membrane 33 never comes to bear against either opposite wall of the casing between two successive regulating phases.

A variant of the above method, in which the position of the membrane 33 in the casing can be adjusted whatever its initial position, is as follows.

Prior to the regulating phase proper, the pump 41 is run in order that the pressures on both sides of the valve 43, as measured by pressure sensors 38, 45, are substantially equal, i.e. the pressure in the second compartment 32 of the casing 30 and the pressure in the pipe 42 connecting the pump 41 to the valve 43. When the balance of the pressures is obtained, the valve 43 is opened.

The pump 41 is then set in rotation in order to force air into the second compartment 32 and the pressure therein is continuously measured by the pressure sensor 45. Depending upon the evolution of the pressure, i.e. of the initial position of the membrane 33, the regulating phase is carried out following three different ways:

If the pressure remains substantially constant (plateau pressure) and then increases up to a predetermined relative pressure threshold (plateau pressure+$\Delta$P) or if, in less than a predetermined period of time T1, the pressure reaches a plateau and then increases up to a relative predetermined pressure threshold (plateau pressure+$\Delta$P), when the predetermined threshold is reached, the sense of rotation of the pump 41 is reversed and the pump is run for a predetermined period of time T4.

If the pressure increases and reaches, before a predetermined period of time T2 has elapsed, a predetermined absolute upper pressure threshold Pmax, the sense of rotation of the pump 41 is reversed and the pump 41 is run until the pressure reaches a predetermined relative pressure threshold (plateau pressure–$\Delta$P). During this step the pressure decreases, stays substantially constant for a plateau period and decreases again. When the pressure reaches the predetermined pressure threshold (plateau pressure–$\Delta$P), the sense of rotation of the pump 41 is reversed and the pump is run for a predetermined period of time T4.

If the pressure increases and does not reach, before a predetermined period of time T3 has elapsed, a plateau or a predetermined absolute upper pressure threshold Pmax, the sense of rotation of the pump 41 is reversed: depending upon the evolution of the pressure, the regulating phase is carried out according to either one of the following ways:

If the pressure reaches a plateau, the pump 41 is run until the pressure reaches a predetermined relative pressure threshold (plateau pressure–$\Delta$P) and when the predetermined threshold is reached, the sense of rotation of the pump 41 is reversed and the pump is run for a predetermined period of time T4.

If the pressure reaches a predetermined absolute lower pressure threshold Pmin, the sense of rotation of the pump 41 is reversed and the pump 41 is run until the pressure reaches a predetermined relative pressure threshold (plateau pressure+$\Delta$P). During this step the pressure increases, stays substantially constant for a plateau period and increases again.

When the predetermined relative threshold is reached, the sense of rotation of the pump 41 is reversed and the pump is run for a predetermined period of time T4.

According to this regulating method, whatever the value of the initial pressure, i.e. whatever the position of the membrane at the starting up of the regulating phase, a plateau pressure is first sought and then the pump 41 is run until the pressure reached a predetermined relative pressure threshold (plateau pressure+ΔP or plateau pressure−ΔP). When this threshold is reached, the sense of rotation of the pump 41 is reversed and the pump is run for a predetermined period of time.

In the alternative, the pump may be operated by a stepper motor; in which case for each of the above operations where the pump is run for a predetermined period of time, it may be run for a predetermined number of steps instead.

T4 can be determined empirically taking into account the shape and internal volume of the casing and the working conditions of the pressure measurement device. In one embodiment of the invention, T1, T2, T3 are chosen equal.

Once the device has been regulated, the valve 44 is again closed and the casing 30 is isolated from the pump 41.

All these steps of the method for regulating the device according to the invention which have been described are preferably controlled and sequenced by the computation and control unit 27 which comprises a microprocessor and the memory capacity which are necessary for storing the program for running the regulation and the top and bottom threshold values used.

Figure 4:
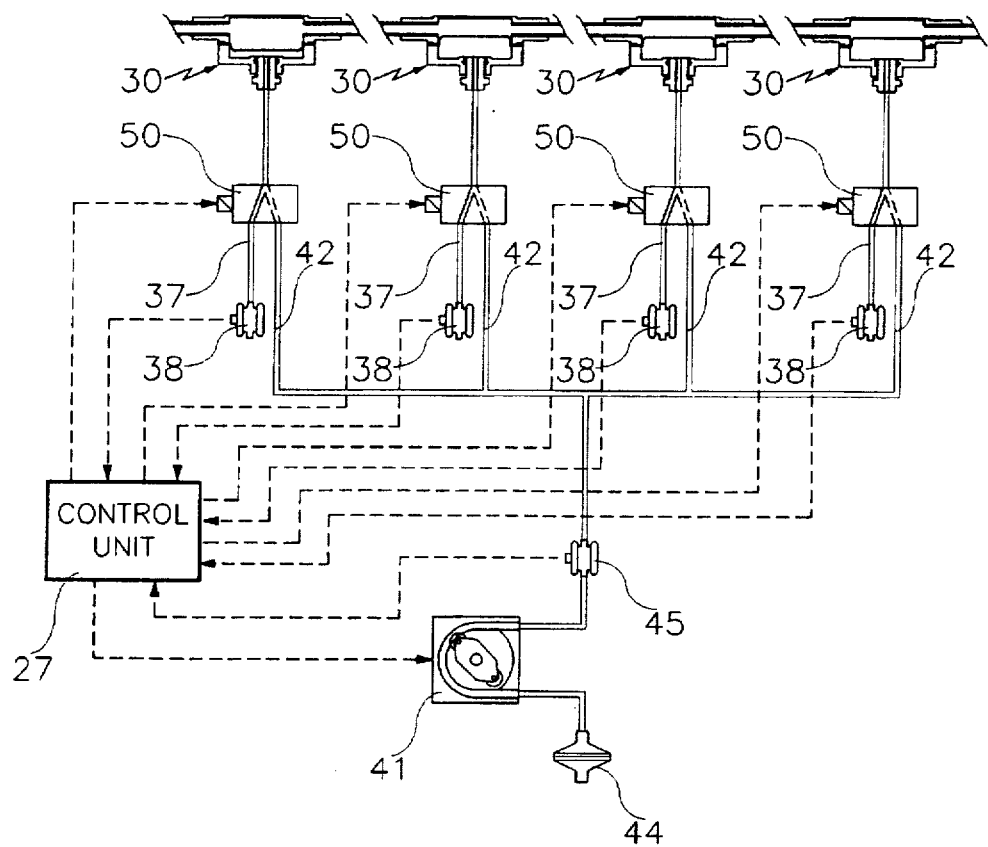
FIG. 4 is a schematic diagram of a pneumatic circuit joining a plurality of pressure devices, illustrated in FIG. 2.

FIG. 4 represents a particular arrangement of the pressure measurement devices of the apparatus represented in FIG. 1. In this arrangement, the pump 41 and the regulating pressure sensor 45 are common to all four pressure measurement devices 23, 24, 25, 26. In contrast to the device of FIG. 2, each of these devices comprises a three-way valve 50 making it possible selectively to connect the second compartment 32 of the casing 30 to the measurement sensor 38 or the second compartment 32 of the casing 30 to the pump 41 and the regulating sensor 45. By virtue of this mounting arrangement, it is possible to check that the measurement sensor 38 is functioning by comparing the pressure value measured by the measurement sensor 38 after repositioning the membrane 33 with the pressure value measured by the regulating sensor 45 during periods I or IV.

The functioning of these devices is not different from that which has just been explained with reference to FIGS. 3 and 4. The regulating phases of the various devices are controlled sequentially, one after the other, according to a program stored in the control unit 27.

The invention is susceptible of variants and modifications. In particular, the field of the invention also extends to a simplified version of the device represented in FIG. 2, in which the connection tube 36 is connected directly to the pump 41, without the possibility of isolating the pump from the casing 30 by a valve.

What is claimed is:

1. A liquid treatment apparatus, comprising:
   a sensor which is sensitive to a variation in gas pressure and which generates signals indicative of sensed pressures;
   a casing divided into a first compartment and a second compartment by a flexible membrane, the first compartment having at least one orifice for the introduction of the liquid, and the second compartment being connectable in a leaktight manner to the pressure sensor;
   pumping means for varying a quantity of gas in the second compartment; and
   means for controlling the pumping means as a function of variations in pressure generated in the second compartment by the pumping means, the controlling means being configured to receive signals from said sensor and to cause, through the pumping means, at least two successive pressure variations, having opposite directions, in the second compartment so as to adjust said position of the membrane between a wall of the casing bounding the first compartment and a wall of the casing bounding the second compartment.

2. An apparatus according to claim 1, wherein the liquid treatment apparatus is a device for measuring liquid pressure.

3. An apparatus according to claim 1, wherein the second compartment is selectively connectable between the pressure sensor and the pumping means.

4. An apparatus according to claim 1, further including a conduit and a valve flow-connected thereto, wherein the pumping means is connectable to the second compartment of the casing by the conduit which can be closed by the valve.

5. An apparatus according to claim 4, further comprising a second pressure sensor connected to the conduit joining the valve to the pumping means.

6. An apparatus according to claim 5, further comprising means for comparing data measured by each of the pressure sensors and for driving the pumping means, so that pressures in the conduit on either side of the valve are substantially equal.

7. An apparatus according to claim 1, wherein the pumping means comprises a pump capable of suction and delivery alternately via two orifices, a first orifice being connected to the atmosphere via a filter and a second orifice being connectable to the second compartment of the casing.

8. A liquid treatment apparatus, comprising:
   a plurality of conduits for circulation of at least one liquid; and
   at least two devices for measuring liquid pressure in at least one conduit, each device including:
      a pressure sensor which is sensitive to a variation in gas pressure;
      a casing divided into a first compartment and a second compartment by a flexible membrane, the first compartment having at least one orifice for liquid introduction and the second compartment being connectable in a leaktight manner to the pressure sensor;
   pumping means for varying a quantity of gas in the second compartment; and
   control means for driving the pumping means as a function of variations of pressure generated in the second compartment by the pumping means, the control means being configured to receive signals from said sensor and to cause, through the pumping means, at least two successive pressure variations, having opposite directions, in the second compartment so as to adjust said position of the membrane between a wall of the casing bounding the first compartment and a wall of the casing bounding the second compartment.

9. An apparatus according to claim 8, wherein the liquid treatment apparatus id designed to treat extracorporeally circulating blood.

10. An apparatus according to claim 8, wherein said plurality of conduits includes:
   a blood withdrawal conduit configured for connecting a patient's arterio-venous system to an inlet of a blood treatment device; and
   a blood return conduit configured for connecting the patient's arterio-venous system to an outlet of the blood treatment device;
   and wherein said at least two liquid pressure measuring devices include:

a pressure measuring device for measuring pressure in the withdrawal conduit; and a pressure measuring device for measuring pressure in the return conduit.

11. An apparatus according to claim 10, further comprising a circulation pump arranged in the withdrawal conduit and two pressure measurement devices for measuring blood pressure in the withdrawal conduit respectively upstream and downstream of the circulation pump.

12. An apparatus according to claim 10, wherein the blood treatment device is a semipermeable-membrane exchanger having a first chamber to which the blood withdrawal conduit and return conduit are connected, and a second chamber to which a treatment liquid supply conduit and a spent liquid discharge conduit are connected, the spent liquid discharge conduit being equipped with a pressure measurement device.

13. An apparatus according to claim 8, wherein the pumping means comprises a pump capable of suction and delivery alternately via two orifices, a first orifice being communicative with the atmosphere via a filter and a second orifice being connectable to the second compartment of the casing.

14. A method for regulating a liquid treatment device, the device including a sensor which is sensitive to a variation in gas pressure, and a casing divided into a first compartment and a second compartment by a flexible membrane, the first compartment having an orifice for introduction of liquid and the second compartment being connectable in a leaktight manner to the pressure sensor, the method comprising the steps of:

introducing a liquid whose pressure is to be measured into the first compartment;

sensing with the sensor variations in gas pressure in the second compartment and generating signals indicative thereof; and varying a quantity of gas in the second compartment as a function of variations in said pressure signals so that the second compartment contains a quantity of gas corresponding to a determined position of the membrane in the casing.

15. A method according to claim 14, where the liquid treatment device is for measuring liquid pressure.

16. A method according to claim 14, wherein the step of varying a quantity of gas in the second compartment comprises the substeps of:

varying a quantity of gas in the second compartment in a first direction until the pressure of the gas reaches a determined initial threshold value; and adjusting the position of the membrane in the casing by varying a quantity of gas in the second compartment in a second direction, opposite the first direction.

17. A method according to claim 14, wherein the step of varying a quantity of gas in the second compartment comprises the substeps of:

varying a quantity of gas in the second compartment until the gas pressure in the second compartment reaches a plateau pressure corresponding to a floating position of the membrane, and then evolves in a first direction to reach a determined threshold value; and adjusting a position of the membrane in the casing by varying a quantity of gas in the second compartment in a second direction, opposite the first direction.

18. A method according to claim 17, wherein the step of varying the quantity of gas in the second compartment until the pressure of the gas in the second compartment reaches a plateau pressure includes the substep of varying in a single direction a quantity of gas in the second compartment.

19. A method according to claim 16, wherein the step of varying the quantity of gas in the second compartment in the second direction is stopped when gas pressure in the second compartment reaches a second determined threshold value.

20. A method according to claim 17, wherein the step of varying the quantity of gas in the second compartment until the pressure of the gas in the second compartment reaches a plateau pressure comprises the steps of:

varying the quantity of gas in the second compartment in the first direction until the pressure of the gas reaches a determined absolute threshold value (Pmax, Pmin), whenever this absolute threshold value (Pmax, Pmin) is reached in less than a predetermined period of time; and varying the quantity of gas in the second compartment in the second direction.

21. A method according to claim 17, wherein the step of varying a quantity of gas in the second compartment until the pressure of the gas in the second compartment reaches a plateau pressure comprises the steps of:

varying a quantity of gas in the second compartment in the first direction for a predetermined period of time; and varying a quantity of gas in the second compartment in a second direction opposite the first direction.

22. A method according to claim 17, wherein the step of varying a quantity of gas in the second compartment until the pressure of the gas in the second compartment reaches a plateau pressure comprises the steps of:

varying a quantity of gas in the second compartment in the first direction for a predetermined period of time;

varying a quantity of gas in the second compartment in the second direction until a pressure of the gas reaches a determined absolute threshold value (Pmax, Pmin); and further varying a quantity of gas in the second compartment in the second direction.

23. A method according to one of claim 16, wherein the step of adjusting the position of the membrane in the casing includes the substep of altering a quantity of gas in the second compartment over a predetermined period of time.

24. A method according to one of claims 19 or 23, further comprising the step of calculating a time period during which gas quantity in the second compartment is altered, the time period corresponding an elapsed period of time between a pressure measurement at the initial threshold value and a pressure measurement at the second threshold value.

25. A method according to one of claims 14, 16, 17, 18, 19, 20, 21, 22, 23, or 15, wherein a pump, operating at a substantially constant flow rate, is used to perform the step of varying a quantity of gas in the second compartment.

26. A method according to one of claims 16, 19, 23, or 15, wherein a pressure value used as a reference for starting the step of adjusting the position of the membrane in the casing is calculated in terms of pressure variation (+P, −P) from a pressure value measured in the second compartment of the casing before the step of varying the quantity of gas in the second compartment.

* * * * *

UNITED STATES PATENT AND TRADEMARK OFFICE
CERTIFICATE OF CORRECTION

PATENT NO. : 5,722,399
DATED : March 3, 1998
INVENTOR(S) : Jacques Chevallet, et al.

It is certified that error appears in the above-indentified patent and that said Letters Patent is hereby corrected as shown below:

Claim 9, Column 8, line 55, "id" should read --is--.

Claim 11, Column 9, line 8, after "conduit" insert -- , --.

Claim 15, Column 9, line 42, "where" should read --wherein--.

Signed and Sealed this

Fourteenth Day of July, 1998

Attest:

BRUCE LEHMAN

Attesting Officer

Commissioner of Patents and Trademarks